United States Patent [19]

Reed

[11] Patent Number: 4,609,578

[45] Date of Patent: Sep. 2, 1986

[54] RESIN-COATED EXTENSIBLE HEAT-SET FIBERGLASS KNIT TAPE

[75] Inventor: Katherine E. Reed, Grant Township, Washington County, Minn.

[73] Assignee: Minnesota Mining and Manufacturing Company, St. Paul, Minn.

[21] Appl. No.: 668,881

[22] Filed: Nov. 6, 1984

[51] Int. Cl.$^4$ ................................................ B32B 7/00
[52] U.S. Cl. ..................................... 428/76; 427/289; 427/314; 427/389.8; 428/251; 428/253; 428/254
[58] Field of Search ................. 428/76, 251, 253, 254; 427/289, 293, 314, 389.8

[56] References Cited

U.S. PATENT DOCUMENTS

| | | | |
|---|---|---|---|
| 3,686,725 | 8/1972 | Nisbet et al. | 28/74 |
| 3,787,272 | 1/1974 | Nisbet et al. | 161/89 |
| 3,793,686 | 2/1974 | Nisbet et al. | 28/75 |
| 3,881,473 | 5/1975 | Corvi et al. | 128/90 |
| 4,134,397 | 1/1979 | Gianakakos et al. | 128/90 |
| 4,376,438 | 3/1983 | Straube et al. | 128/90 |
| 4,433,680 | 2/1984 | Yoon | 128/90 |

FOREIGN PATENT DOCUMENTS 8100671  3/1981  PCT Int'l Appl. .

OTHER PUBLICATIONS

"Textile Fibers for Industry" Publication No. 5-TO-D-8285-B Litho U.S.A., Feb. 1983, Owens Corning Fiberglas Corp.

*Primary Examiner*—Marion C. McCamish
*Attorney, Agent, or Firm*—Donald M. Sell; James A. Smith; Carolyn A. Bates

[57] ABSTRACT

An improved resin-coated fiberglass knit tape is disclosed which is highly extensible in the lengthwise direction and heat-set to alleviate fraying at cut ends. Heat-setting with essentially no tension on the tape accounts for retention of good extensibility. The invention is especially applicable to the field of orthopedic casting tape.

7 Claims, No Drawings

RESIN-COATED EXTENSIBLE HEAT-SET FIBERGLASS KNIT TAPE

FIELD OF THE INVENTION

This invention relates to the field of knitted fiberglass fabrics. More particularly, it relates to extensible knitted fiberglass fabrics which are coated or impregnated with a liquid resin which cures to form rigid reinforced fiberglass articles. Another aspect of the invention relates to a method of forming such resin-coated or impregnated fiberglass fabrics. A preferred embodiment of the invention relates to orthopedic casting tapes comprising resin-coated or impregnated, extensible, knitted fiberglass.

BACKGROUND ART

High modulus fibers such as fiberglass are commonly used as resin reinforcements in composite materials to impart strength to the cured article. In some applications the fiberglass yarn is woven or knit into a fabric which can then be treated with a finish, resin or other coating. Compared to organic fibers such as polyester, glass fibers exhibit virtually no elongation and are more prone to breakage during process operations such as knitting and weaving. Because the fiber elongation is essentially nil, glass fabrics do not stretch unless they are constructed with very loose loops which can deform upon application of tension, thereby giving the impression of stretching. Knitting imparts extensibility by virtue of its system of interlocking knots and loops.

An important usage of knitted fiberglass fabrics is in the manufacture of orthopedic cast bandages where those fabrics are coated or impregnated with a curable resin and packaged as rolls of tape, which are subsequently used by a physician or medical clinician to construct orthopedic casts. When constructing an orthopedic cast from a roll of cast bandage (typically four-inches wide), it is necessary to make tucks or folds to accommodate excess material when changing the direction of wrapping or when going around contours such as the heel of the foot. This requires a high level of skill on the part of the applier to achieve a functional and smooth cast. To eliminate tucks and folds and facilitate application, it is desirable that the bandaging material be extensible. At least 20% and preferably 25%–35% extensibility is necessary in material of four-inch width to conform easily around the heel of a medium size adult.

Prior to the present invention, most commercially-available, resin-coated, knitted fiberglass casting tapes exhibited approximately 5%–15% extensibility beyond their relaxed length. The only product which provided greater extensibility, a product marketed under the trademark "K-Cast" (manufactured by Hexcel Corporation, San Francisco, Calif.), suffered from the problem of fraying along cut edges.

Like most knitted fabrics, fiberglass knits tend to curl or fray at a cut edge as the yarns are severed and adjacent loops unravel. When a segment of yarn is removed from such a fabric and allowed to relax, it remains in the new position in which it is placed. Fraying and raveling produce unsightly ends and, in the case of an orthopedic cast, frayed ends may interfere with the formation of a smooth cast, and loose, frayed ends may be sharp and irritating. Accordingly, frayed edges are considered a distinct disadvantage in orthopedic casting tapes.

It is well-known that fraying of fiberglass knits at cut edges can be prevented by passing the fabric through a heat cycle which sets the yarns giving them new three-dimensional configurations based on their positions in the knit. Fiberglass fabrics intended to be coated or impregnated with a resin are sometimes put through a heat-setting process for the additional purpose of removing sizing from glass filaments which would otherwise interfere with the proper application of the resin.

A batch process recommended by Owens-Corning Fiberglass Corporation, Toledo, Ohio to remove the sizing on the glass filaments results in a heat-set fabric and consists of the following steps:

1. Start at 220° F. for 1.5 hours;
2. Raise to 480° F. over a period of 5 hours and hold for 12 hours;
3. Raise to 700° F. over a period of 3 hours and hold for 33 hours;
4. Cool to room temperature.

A continuous process involving much less time is also possible.

When a fiberglass fabric which has been heat-set is cut, there is minimal fraying and when a segment of yarn is removed from the fabric and allowed to relax, it curls into the crimped shape in which it was held in the knit. Accordingly, at the site of a cut, the severed yarns have a tendency to remain in their looped or knotted configuration rather than to spring loose.

Thus, the problem of alleviating frayed ends is easily overcome by conventional heat-setting processes. However, as one aspect of the present invention, it has been discovered that conventional heat-setting processes significantly reduce extensibility of fiberglass knits. Thus, prior to the present invention, resin-coated, heat-set (and therefore non-fraying) fiberglass knit tapes exhibiting extensibility of at least 20 percent were not available.

SUMMARY OF THE INVENTION

According to the present invention there is provided a method of forming a storage-stable, resin-coated knitted fiberglass tape having improved extensibility as well as resistance to fraying. This method comprises the steps of (1) heating a length of knitted fiberglass tape having extensibility of at least 22 percent, preferably 25 or 30 percent, essentially without tension in the lengthwise direction, at a temperature and for a time sufficient to set the fabric at least to the extent a ten-inch piece of such tape is set by heating without tension for three minutes at 800° F.; (2) applying a liquid resin to the fiberglass tape which is capable of curing to form a rigid structure; (3) cutting the resin-coated tape into pieces of predetermined lengths suitable for its intended use; and (4) packaging said pieces in a package suitable to prevent curing of the resin prior to the time of use.

Another aspect of the invention is the storage-stable knitted fiberglass tape produced by the aforementioned process comprising (1) a knitted fiberglass tape which has been heat-set to prevent fraying of the cut ends; (2) a liquid resin coated on the tape which is capable of curing to form a rigid structure; and (3) suitable packaging for the resin-coated tape to prevent curing prior to the time of use. The resin-coated tape exhibits an extensibility of at least 20 percent in the lengthwise direction prior to curing.

The preferred embodiment of the present invention is an orthopedic casting tape wherein the liquid resin is a moisture-curable isocyanate-terminated polyurethane prepolymer.

DETAILED DESCRIPTION

In order to obtain the resin-coated, knitted fiberglass tapes of the present invention, it is necessary to start with knitted fiberglass fabric which exhibits at least 22–25 percent extensibility in the lengthwise direction. Even when processed according to the present invention there is a slight loss of extensibility due to dimensional shrinkage (on the order of 2 to 5 percent) of the fabric during the heating step.

To determine extensibility within the context of the present invention, the following method is employed. A 10-inch length of fiberglass tape is placed in the grips of a standard "Instron" Tensile Tester and a load of five pounds applied. The length of the fabric in the stretched position is compared to its length in the unstretched state to determine extensibility. A load of five-pounds was selected as this approximates the maximum tension typically used when applying a synthetic orthopedic casting tape.

Knitted fiberglass fabrics meeting the initial extensibility requirements of the present invention are known. Fiberglass knitted fabrics with good extensibility are achievable with two common knitting methods: Raschel and tricot. Two and three bar Raschel knits can be produced by regulating the amount of yarn in each stitch. Factors which affect the extensibility of fiberglass Raschel knits are the size of the loops in the chain stitch, especially in relation to the diameter(s) of the yarn(s) which passes through them, and the amount of a loose yarn in the layin stitches. If a chain loop is formed and two strands of layin yarn pass through it which nearly fill the loop, then the loop cannot be deformed or elongated and little or no stretch will be observed. Conversely, if the layin yarns do not fill the loop, then application of tension will deform the loop to the limits of the layin yarn diameter and stretch will be observed. Therefore, the larger the chain loop relative to yarn diameter, the greater the stretch. Similarly, the amount of yarn in the layin stitch in excess of that needed to lock the chain rows together is proportional to the imparted stretch. Tricot knits usually result in greater extensibility because their construction allows the openings in the fabric to deform. Typically, as these fabrics are extended in one direction, the fabric narrows in the perpendicular direction. Another basic type of knitting which results in stretchy fabrics is generally called tubular knitting which is commonly employed to knit socks, orthopedic stockinet, etc. A fabric called "Tubular Weave Stockinette" distributed by Otto Bach Orthopedic Industries, Inc., Minneapolis, Minn., is a fiberglass fabric, knit by a Raschel machine and exhibits approximately 50% extensibility in the crosswise direction and approximately 175% extensibility in the lengthwise direction.

For orthopedic casting material, the fiberglass fabric selected, in addition to having the extensibility requirements noted above, should be of a suitable thickness and mesh size to insure good penetration of the curing agent into the roll of resin-coated tape and to provide a finished cast with adequate strength and porosity. Such fabric parameters are well-known to those skilled in the art and are described in U.S. Pat. No. 4,502,478.

In processing the knitted fiberglass fabric of the present invention, a length of fabric is heat-set essentially without tension. Preferably, the fabric is wound onto a cylindrical core so large batches can be processed at one time in a single oven. Care must be taken to avoid applying undue tension to the fabric which would distort the knots and loops. Prior to the present invention, rolls of moving webs of fabric were typically wound with some degree of tension so that the roll would not telescope and the web could be steered and uniformly processed. To prevent applying tension to the fabric during winding, the winding operation must be performed with a sag in the fabric as it is wound on the core.

A continuous heating-setting process may also be used in which a length of fabric is placed without undue tension on a moving conveyor system and passed through an oven for sufficient time and temperature to achieve heat setting of the fabric.

The heat-setting step may be performed in a number of conventional ways known to the art. In heat-setting a small piece of fabric, e.g., 10 inches of tape, in a single layer, a temperature of 800° F. for three minutes has been found to be sufficient. To achieve optimum setting, a temperature of 1000° F. for three minutes is required. Equivalent setting at lower temperatures is possible, but longer time is required. Batch processes require a longer residence time at the selected temperature due to the mass of glass fabric which must be heated.

The optimum heat-setting process described above is sufficient in most cases to remove the sizing from the fabric. However, the process of the present invention may also be practiced using partially heat-desized or a chemically-desized fabric. Chemical desizing processes are described in U.S. Pat. Nos. 3,686,725; 3,787,272; and 3,793,686.

The fabric is preferably cooled prior to application of the resin.

The resin selected to apply to the heat-set fabric is dictated by the end-use of the product. For orthopedic casting materials, suitable resins are well-known and described for example, in U.S. Pat. Nos. 4,376,438, 4,433,680 and 4,502,479. The preferred resins are the moisture-curable isocyanate-terminated polyurethane prepolymers described in the aforementioned patents. The amount of such resin applied to the fiberglass tape to form an orthopedic casting material is typically an amount sufficient to constitute 35 to 50 percent by weight of the final "coated" tape. The term "coated" or "coating" as used herein with respect to the resin refers generically to all conventional processes for applying resins to fabrics and is not intended to be limiting.

To insure storage stability of the coated tape, it must be properly packaged, as is well-known in the art. In the case of water-curable isocyanate-terminated polyurethane prepolymer resin systems, moisture must be excluded. This is typically accomplished by sealing the tape in a foil or other moisture-proof pouch.

In addition to the application of the present invention to the field of orthopedic casting tapes, other uses may include wrapping and/or joining pipes, cables or the like; making molds; patching or bridging gaps to provide a surface for filling and repairs; etc.

The invention may be further illustrated by the following working example which is merely illustrative and not intended to be limiting in any way.

EXAMPLE

Fiberglass tape is knit on a Raschel warp knitter using ECD-E 75 1/0 1.0Z fiberglass yarn. The fabric is a 2 bar, 18 gauge construction consisting of an open chain stitch and a layin stitch which overlaps 4 needles. The fabric characteristics are: 13 wales per inch; 15.5 courses per inch; chain stitch runner length of 145 inches; layin stitch runner length of 146 inches. A relaxed section of tape 10 inches in length can be extended to a length of 13.25 inches when manually held taut (32.5% stretch). The tape is wound on a metal core into a roll which contains about 200 linear yards of tape. The winding operation is performed with a sag in the tape as it is rolled onto the core. Therefore, there is essentially no tension applied to the tape. The loose roll of fiberglass tape is then placed in a cool oven. The oven is closed, then set for 440° F. After 1 hour and 15 minutes the oven is set for 1000° F. After 8 hours the heat is turned off and the oven remains closed and is allowed to cool for 12 hours. The tape is then removed from the oven. A relaxed section of tape 10 inches in length can be extended to a length of 12.75 inches when manually held taut (27.5% extensibility). The roll is placed on a motorized spindle, and the tape is fed over a roller and rewound on another spindle. At the roller station a liquid isocyanate-terminated polyurethane prepolymer resin is extruded onto the tape so that the coated tape is 40% by weight resin. The unwind and windup tensions are adjusted to a minimum but no sag is present. The coated roll is removed to another spindle which is free-wheeling. The leading edge of the tape is wrapped over a plastic core which is then spun slowly until 4 yards of tape is wound onto the core. The rolling operation is also under minimum tension so the coated tape is not stretched as it is taken up by the core. The four-yard roll of tape is then packaged in a plastic/aluminum laminate pouch impervious to water which is heat-sealed. Tape removed from the pouch exhibits 27.5% extensibility in the lengthwise direction.

What is claimed is:

1. A storage-stable, resin-coated, knitted fiberglass tape comprising:
   a. a knitted fiberglass tape which has been heat-set essentially without tension to prevent fraying of cut ends of said tape;
   b. a liquid resin coated on said tape capable of curing to form a rigid article; and
   c. a package for said tape suitable to prevent curing of said resin prior to the time of use;
   said resin-coated tape having an extensibility of at least 20 percent in the lengthwise direction prior to curing.

2. The fiberglass tape according to claim 1 wherein said liquid resin is a water-curable isocyanate-terminated polyurethane prepolymer.

3. The fiberglass tape according to claim 2 wherein said package is moisture-proof.

4. The fiberglass tape according to claim 1 wherein said resin-coated tape exhibits extensibility between 25 and 35 percent prior to curing.

5. A method of forming a storage-stable, resin-coated knitted fiberglass tape having improved extensibility and resistance to fraying comprising:
   a. heating a length of knitted fiberglass tape having extensibility of at least 22 percent in the lengthwise direction essentially without tension for a time sufficient to set said fabric at least to the extent a ten-inch length of said fabric is set by heating at 800° F. for 3 minutes;
   b. coating said fiberglass tape with a liquid resin;
   c. cutting said resin-coated tape into lengths suitable for the intended use of the tape; and
   d. packaging said resin-coated tape in a package suitable to prevent the curing of said resin prior to the time of use;
   whereby said resin-coated tape has an extensibility of at least 20 percent in the lengthwise direction prior to curing.

6. The method according to claim 5, wherein said length of knitted fiberglass tape is first wound onto a cylindrical core essentially without tension.

7. The method of claim 5, wherein said fabric is heated to set said fabric at least to the extent a 10-inch piece of said fabric is set by heating at 1000° F. for 3 minutes.

* * * * *

UNITED STATES PATENT AND TRADEMARK OFFICE
CERTIFICATE OF CORRECTION

PATENT NO. : 4,609,578

DATED : September 2, 1986

INVENTOR(S) : Katherine E. Reed

It is certified that error appears in the above-identified patent and that said Letters Patent is hereby corrected as shown below:

Col. 3, line 62, "4,502,478" should be --4,502,479--.

Signed and Sealed this

Eleventh Day of November, 1986

Attest:

DONALD J. QUIGG

Attesting Officer

Commissioner of Patents and Trademarks